(12) United States Patent
Nantermet et al.

(10) Patent No.: US 8,008,315 B2
(45) Date of Patent: Aug. 30, 2011

(54) BENZYLETHER AND BENZYLAMINO BETA-SECRETASE INHIBITORS FOR THE TREATMENT OF ALZHEIMER'S DISEASE

(75) Inventors: Philippe G. Nantermet, Lansdale, PA (US); Hemaka Anthony Rajapakse, Wyncote, PA (US); Harold G. Selnick, Ambler, PA (US)

(73) Assignee: Merck, Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 12/772,711

(22) Filed: May 3, 2010

(65) Prior Publication Data

US 2010/0210693 A1    Aug. 19, 2010

Related U.S. Application Data

(62) Division of application No. 10/573,232, filed on Mar. 23, 2006, now Pat. No. 7,829,597.

(51) Int. Cl.
*A01N 43/40* (2006.01)
*A61K 43/42* (2006.01)
*C07D 295/00* (2006.01)

(52) U.S. Cl. ............................. 514/277; 544/1; 544/184

(58) Field of Classification Search .............. 546/1, 184; 514/277
See application file for complete search history.

*Primary Examiner* — Paul V. Ward
(74) *Attorney, Agent, or Firm* — Keith D. MacMillan; Gerard M. Devlin

(57) ABSTRACT

The present invention is directed to compounds which are inhibitors of the beta-secretase enzyme and that are useful in the treatment of diseases in which the beta-secretase enzyme is involved, such as Alzheimer's disease. The invention is also directed to pharmaceutical compositions comprising these compounds and the use of these compounds and compositions in the treatment of such diseases in which the beta-secretase enzyme is involved.

20 Claims, No Drawings

BENZYLETHER AND BENZYLAMINO BETA-SECRETASE INHIBITORS FOR THE TREATMENT OF ALZHEIMER'S DISEASE

CROSS-REFERENCE TO RELATED APPLICATIONS

This is a Divisional application of U.S. patent application Ser. No.: 10/573,232, which entered U.S. National examination via 35 U.S.C. §371 on Mar. 23, 2006, now allowed, which claims the benefit of priority to U.S. Provisional Application No. 60/508,369 filed Oct. 2, 2003, expired, each of which is incorporated by reference as if fully set forth herein.

BACKGROUND OF THE INVENTION

Alzheimer's disease is characterized by the abnormal deposition of amyloid in the brain in the form of extra-cellular plaques and intra-cellular neurofibrillary tangles. The rate of amyloid accumulation is a combination of the rates of formation, aggregation and egress from the brain. It is generally accepted that the main constituent of amyloid plaques is the 410 amyloid protein (βA4, also referred to as Aβ, β-protein and βAP) which is a proteolytic product of a precursor protein of much larger size. The amyloid precursor protein (APP or AβPP) has a receptor-like structure with a large ectodomain, a membrane spanning region and a short cytoplasmic tail. The Aβ domain encompasses parts of both extra-cellular and transmembrane domains of APP, thus its release implies the existence of two distinct proteolytic events to generate its $NH_2$- and COOH-termini. At least two secretory mechanisms exist which release APP from the membrane and generate soluble, COOH-truncated forms of APP ($APP_S$). Proteases that release APP and its fragments from the membrane are termed "secretases." Most $APP_S$ is released by a putative α-secretase which cleaves within the Aβ protein to release α-$APP_S$ and precludes the release of intact Aβ. A minor portion of $APP_S$ is released by a β-secretase ("β-secretase"), which cleaves near the $NH_2$-terminus of APP and produces COOH-terminal fragments (CTFs) which contain the whole Aβ domain.

Thus, the activity of β-secretase or β-site amyloid precursor protein-cleaving enzyme ("BACE") leads to the abnormal cleavage of APP, production Aβ, and accumulation of (3 amyloid plaques in the brain, which is characteristic of Alzheimer's disease (see R. N. Rosenberg, Arch. Neurol., vol. 59, September 2002, pp. 1367-1368; H. Fukumoto et al, Arch. Neurol., vol. 59, September 2002, pp. 1381-1389; J. T. Huse et al, J. Biol. Chem., vol 277, No. 18, issue of May 3, 2002, pp. 16278-16284; K. C. Chen and W. J. Howe, Biochem. Biophys. Res. Comm, vol. 292, pp 702-708, 2002). Therefore, therapeutic agents that can inhibit β-secretase or BACE may be useful for the treatment of Alzheimer's disease.

The compounds of the present invention are useful for treating Alzheimer's disease by inhibiting the activity of β-secretase or BACE, thus preventing the formation of insoluble Aβ and arresting the production of Aβ.

SUMMARY OF THE INVENTION

The present invention is directed to compounds that are inhibitors of the β-secretase enzyme, and that are useful in the treatment of diseases in which the β-secretase enzyme is involved, such as Alzheimer's disease. The invention is also directed to pharmaceutical compositions comprising these compounds and the use of these compounds and compositions in the treatment of such diseases in which the β-secretase enzyme is involved.

DETAILED DESCRIPTION OF THE INVENTION

The present invention is directed to compounds of the formula (I):

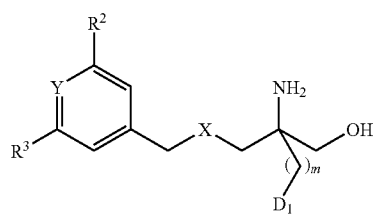

wherein:
X is O or NH;
Y is CH or N;
$R^1$ is (1) aryl selected from the group consisting of phenyl and napthyl, or
  (2) heterocyclyl selected from the group consisting of piperazinyl, piperidinyl, pyrrolidinyl, pyrazinyl, dihydropyrazinyl, pyrazolyl, dihydropyrazolyl, pyridazinyl, pyridyl, dihydropyridinyl, pyrimidinyl, dihydropyrimidinyl, pyrrolyl, dihydropyrrolyl, tetrazolyl, dihydrotetrazolyl, furanyl, dihydrofuranyl, tetrahydrofuranyl, imidazolyl, dihydroimidazolyl, triazinyl, pyranyl, tetrahydropyranyl, thiazolyl, thienyl, dihydrothienyl, thiophenyl, triazolyl, dihydrotriazolyl, morpholinyl, thiomorpholinyl, dihydrothiadiazolyl, tetrahydrothienyl, oxazolyl, isoxazolyl, thiazolyl, oxadiazolyl, indolyl, quinolinyl, isoquinolinyl, benzimidazolyl and benzoxazolyl,
wherein said aryl or heterocyclyl is unsubstituted or substituted with one or more
  (a) halo,
  (b) —$C_{1-6}$alkyl,
  (c) —$C_{2-6}$ alkenyl,
  (d) —$C_{2-6}$ alkynyl,
  (e) —OH,
  (f) —CN, or
  (g) —O—$C_{1-6}$alkyl;
$R^2$ is selected from the group consisting of:
  (1) $R^4$—S(O)$_2$N($R^7$)—, wherein $R^4$ is $C_{1-6}$alkyl, wherein said alkyl is unsubstituted or substituted with one or more
    (a) halo,
    (b) —$C_{1-6}$alkyl,
    (c) —OH,
    (d) —CN, or
    (e) —O—$C_{1-6}$alkyl; and
  $R^7$ is selected from the group consisting of
    (a) hydrogen, and
    (b) —$C_{1-6}$alkyl,
    wherein said alkyl is unsubstituted or substituted with one or more
      (i) halo,
      (ii) —$C_{1-6}$alkyl,
      (iii) —OH,
      (iv) —CN, or
      (v) —O—$C_{1-6}$alkyl;

(2)

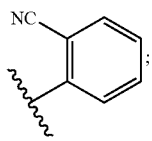

and (3)

$R^3$ is selected from the group consisting of:

(a)

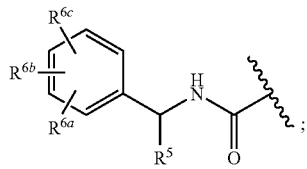

(b)

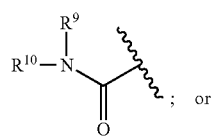
; or (c)

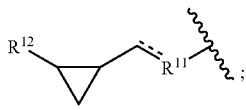
;

wherein $R^5$ is $C_{1-6}$alkyl, $C_{2-6}$ alkenyl or $C_{2-6}$ alkynyl;
$R^{6a}$, $R^{6b}$, and $R^{6c}$ are independently selected from the group consisting of:
(1) hydrogen,
(2) halo,
(3) —$C_{1-6}$alkyl,
(4) —$C_{2-6}$ alkenyl,
(5) —$C_{2-6}$ alkynyl,
(6) —OH,
(7) —CN, and
(8) —O—$C_{1-6}$alkyl;
$R^9$ and $R^{10}$ are independently selected from the group consisting of:
(1) hydrogen,
(2) —$C_{1-6}$alkyl,
(3) —$C_{2-6}$ alkenyl, and
(4) —$C_{2-6}$ alkynyl,
or $R^9$ and $R^{10}$ are joined together with the nitrogen atom to which they are attached to form a pyrrolidine ring, which is optionally substituted with
(a) —$C_{1-6}$alkyl,
(b) —$C_{2-6}$ alkenyl,
(c) —$C_{2-6}$ alkynyl,
(d) $(CH_2)_n$-phenyl, or
(e) $(CH_2)_n$-furanyl;

wherein said alkyl, phenyl and furanyl are unsubstituted or substituted with one or more
i) halo,
ii) —$C_{1-6}$alkyl,
iii) —OH,
iv) —CN, or
v) —O—$C_{1-6}$alkyl; and
$R^{11}$ is selected from the group consisting of
(1) —CH—,
(2) —O—, and
(3) —NH—,
provided that when $R^{11}$ is —CH— the dotted line forms a bond and when $R^{11}$ is —O— or —NH— the dotted line is absent;
$R^{12}$ is hydrogen, $C_{1-6}$ alkyl, $C_{2-6}$ alkenyl or $C_{2-6}$ alkynyl;
m is 1 or 2;
n is 0, 1, 2, 3 or 4;
p is 1, 2, 3 or 4;
and pharmaceutically acceptable salts thereof.

In one embodiment of the compounds of formula (I), m is 1 and $R^1$ is phenyl, unsubstituted or substituted in one or two positions with halo, preferably with fluoro or chloro. In another embodiment, m is 2 and $R^1$ is phenyl, unsubstituted or substituted in one or two positions with halo, preferably with fluoro or chloro. In another embodiment, m is 1 and $R^1$ is thiophenyl.

In another embodiment of the compounds of formula (I), $R^2$ is $R^4$—$S(O)_2N(R^7)$—, wherein $R^4$ and $R^7$ are each $C_{1-6}$alkyl, for example are each methyl.

In another embodiment of the compounds of formula (I), $R^2$ is

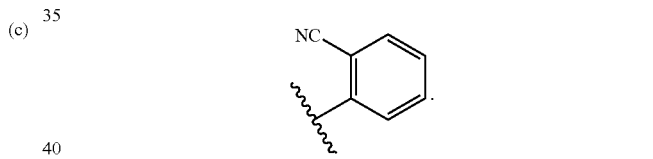

In another embodiment of the compounds of formula (I), X is O.

In another embodiment of the compounds of formula (I), Y is CH.

An embodiment of the present invention is directed to compounds of the formula II:

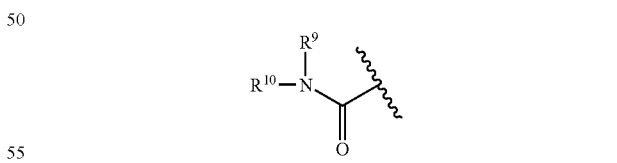

wherein X, Y, $R^1$, $R^2$, $R^5$, $R^{6a}$, $R^{6b}$, $R^{6c}$ and m are as defined herein,
and pharmaceutically acceptable salts thereof.

In one embodiment of the compounds of formula (II), $R^5$ is methyl. In another embodiment of the compounds of formula (II), $R^{6a}$ and $R^{6b}$ are hydrogen and $R^{6c}$ is fluoro.

In another embodiment of the compounds of formula (II), X is O.

In another embodiment of the compounds of formula (II), Y is CH.

Another embodiment of the present invention is directed to compounds of the formula (III):

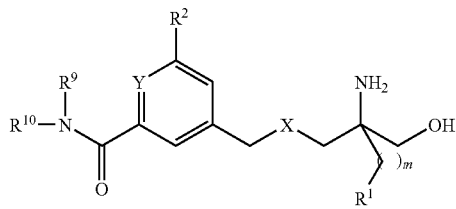

wherein X, Y, $R^1$, $R^2$, $R^9$, $R^{10}$ and m are as defined herein.

In another embodiment of the compounds of formula (III), $R^9$ and $R^{10}$ are joined together to form a pyrrolidine ring which is unsubstituted or substituted with $(CH_2)_n$-furanyl wherein n is 0.

In another embodiment of the compounds of formula (III), X is O.

In another embodiment of the compounds of formula (III), Y is CH.

Another embodiment of the present invention is directed to compounds of the formula (IV):

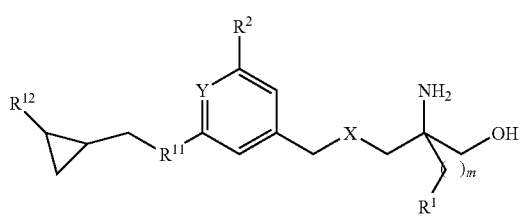

wherein X, $R^1$, $R^2$, $R^{11}$, $R^{12}$ and m are as defined herein.

In an embodiment of the compounds of formula (N), X is O.

In another embodiment of the compounds of formula (N), Y is CH.

Another embodiment of the present invention includes a compound which is selected from the title compounds of the following Examples and pharmaceutically acceptable salts thereof.

As used herein, the term "alkyl," by itself or as part of another substituent, means a straight or branched chain hydrocarbon radical having the number of carbon atoms designated (e.g., $C_{1-6}$ alkyl means an alkyl group having from 1 to 6 carbon atoms). Exemplary alkyl groups include methyl, ethyl, n-propyl, isopropyl, n-butyl, isobutyl, tert-butyl, pentyl, hexyl, and the like.

As used herein, the term "alkenyl," by itself or as part of another substituent, means a straight or branched chain hydrocarbon radical having a single-carbon-carbon double bond and the number of carbon atoms designated (e.g., $C_{2-10}$ alkenyl means an alkenyl group having from two to ten carbon atoms). Preferred alkenyl groups for use in the invention are $C_{2-6}$ alkenyl groups, having from two to six carbon atoms. Exemplary alkenyl groups include ethenyl and propenyl.

As used herein, the term "alkynyl" by itself or as part of another substituent, means a straight or branched chain hydrocarbon radical having a single carbon-carbon triple bond and the number of carbon atoms designated (e.g., $C_{2-10}$ alkynyl means an alkynyl group having from two to ten carbon atoms). Preferred alkynyl groups for use in the invention are $C_{2-6}$ alkynyl groups, having from two to six carbon atoms. Exemplary alkynyl groups include ethynyl and propynyl.

The term "halo" or "halogen" includes fluoro, chloro, bromo and iodo.

The compounds of the instant invention have at least one asymmetric center. Additional asymmetric centers may be present depending upon the nature of the various substituents on the molecule. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of these compounds.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

The compounds of the present invention are prepared by the methods outlined in Scheme 1, below.

In Scheme 1, an alkyl serine derivative of type 1 is converted to the corresponding alcohol 2 which in turn is protected as the Boc derivative 3. Deprotonation and alkylation of diethyl 2-[N-(tert-butoxycarbonyl)-amino]malonate 4 with various alkyl or benzyl bromides, followed by reduction provides an alternative to the preparation of diols of type 3. Boc removal then provides an alternative route to 2. The alkyl serine derivative of type 1 is esterified with MeOH, and protected with Boc, and the hydroxyl group is converted to the corresponding azide which is reduced to afford an amine of type 5.

Scheme 1

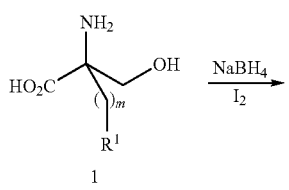

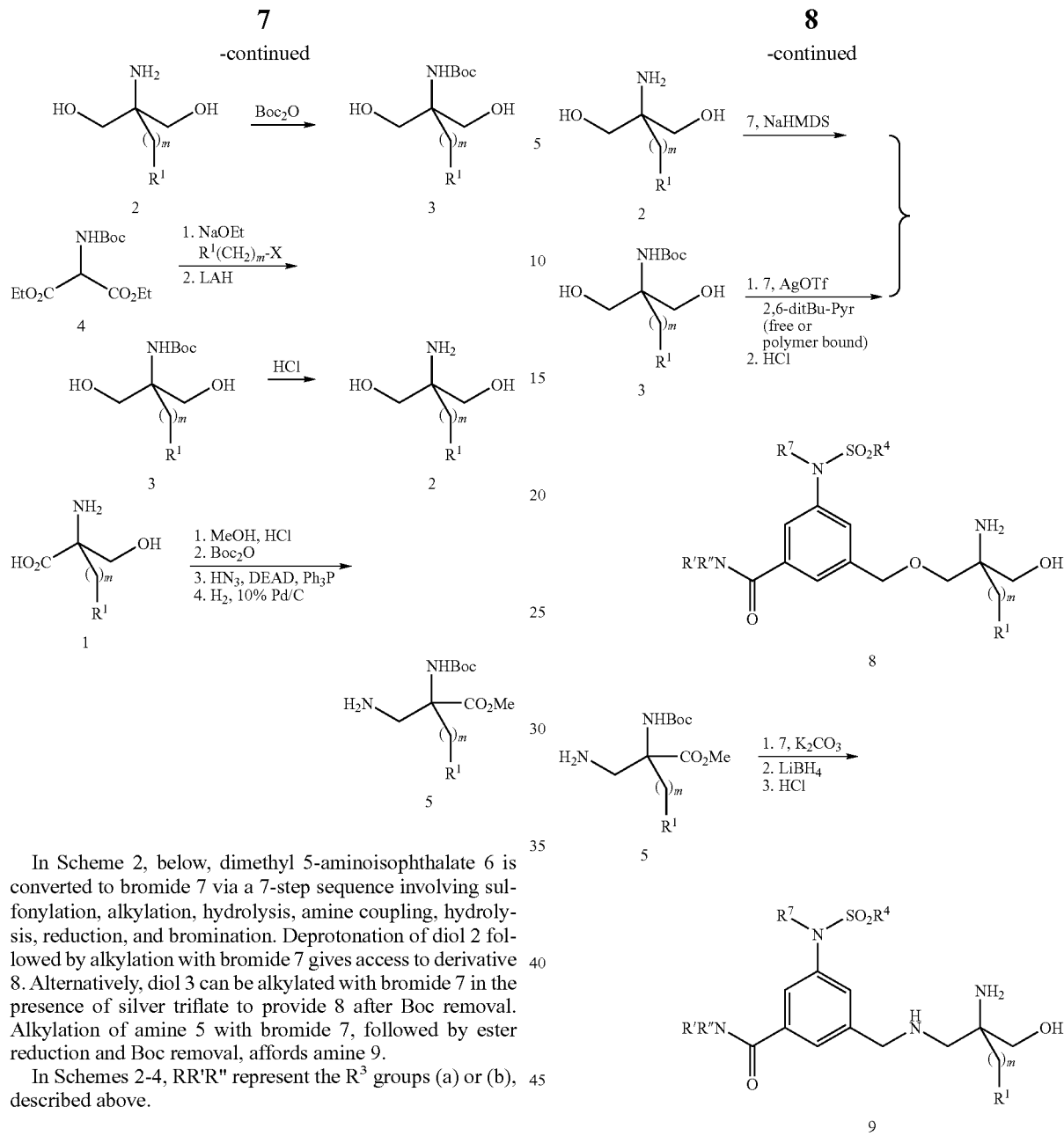

In Scheme 2, below, dimethyl 5-aminoisophthalate 6 is converted to bromide 7 via a 7-step sequence involving sulfonylation, alkylation, hydrolysis, amine coupling, hydrolysis, reduction, and bromination. Deprotonation of diol 2 followed by alkylation with bromide 7 gives access to derivative 8. Alternatively, diol 3 can be alkylated with bromide 7 in the presence of silver triflate to provide 8 after Boc removal. Alkylation of amine 5 with bromide 7, followed by ester reduction and Boc removal, affords amine 9.

In Schemes 2-4, RR'R" represent the $R^3$ groups (a) or (b), described above.

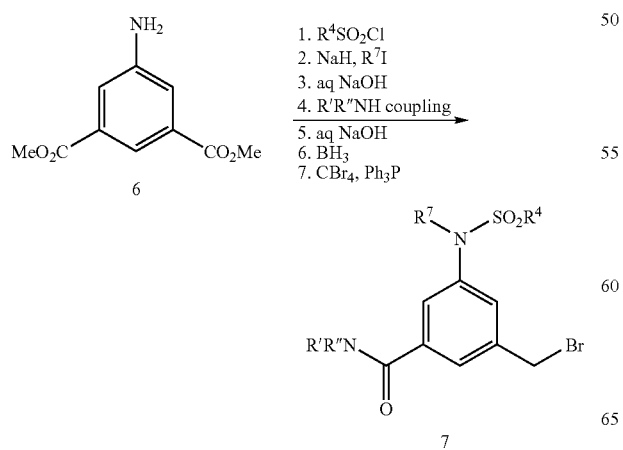

Scheme 3 illustrates the preparation of bromide of type 11 from dimethyl 5-iodoisophthalate 10 via Pd coupling, hydrolysis, reduction and bromination. Alkylation of diol 3 with bromide 11, followed by hydrolysis, amine coupling and Boc removal gives access to ether 12.

Scheme 3 intermediate 17. The cyano-cycloalkyl group is introduced via TMS-CN and the necessary dibromoalkane. Subsequent cyclopropanation provides 18 that is converted to bromide 19. The preparation of bromide 22 relies on similar methodology regarding the $R^{12}$-bearing side chain and a Curtius rearrangement for the introduction of $R^7NSO_2R^4$.

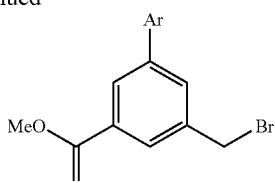

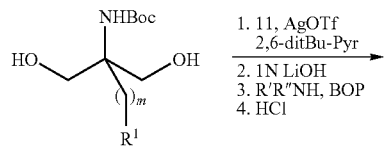

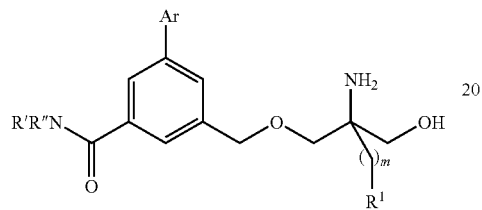

Scheme 4 illustrates the preparation of bromide of type 15 that is then coupled to diol 2 or 3, as described in scheme 2. Installation of both side chains using Pd0 coupling methodology followed by reduction of the ester moiety and subsequent bromination provides 15.

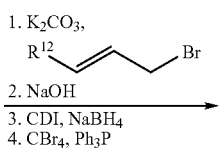

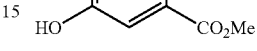

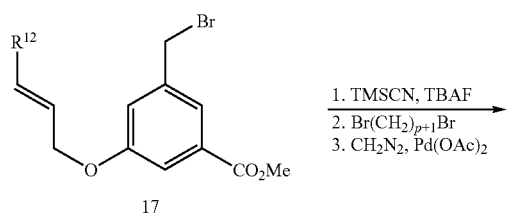

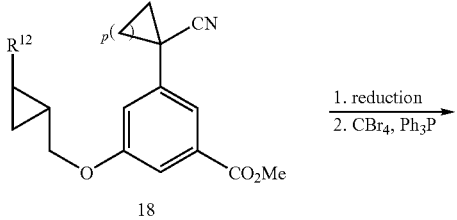

Scheme 5 illustrates the preparation of bromides of type 19 and 22 that are then coupled to diol 2 or 3, as described in scheme 2. Phenol 16 is alkylated and the methyl ester is converted to a bromomethyl functionality giving access to -continued

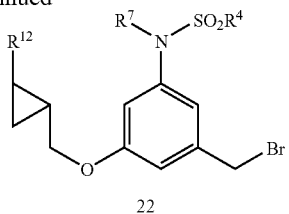

Scheme 6 illustrates two alternative preparations of bromide of type 23 that is then coupled to diol 2 or 3, as described in scheme 2. The first preparation relies on conversion of the methyl ester to an aldehyde and a Wittig coupling to install the $R^5$-bearing alkene. The second preparation is based on an indenium/palladium coupling strategy.

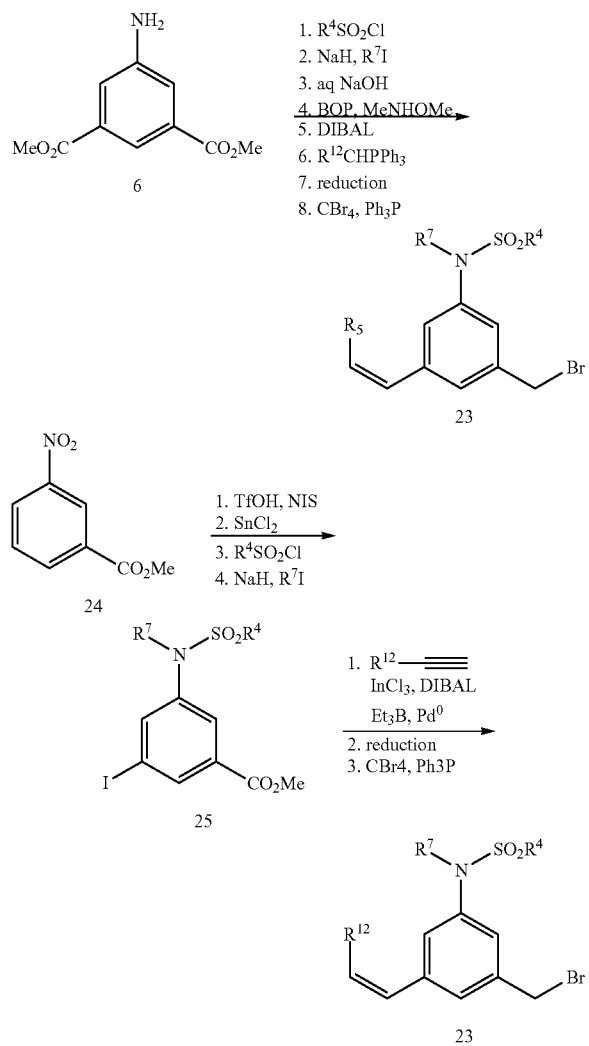

The term "substantially pure" means that the isolated material is at least 90% pure, and preferably 95% pure, and even more preferably 99% pure as assayed by analytical techniques known in the art.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic, trifluoroacetic acid, and the like. Particularly preferred are citric, hydrobromic, hydrochloric, maleic, phosphoric, sulfuric, fumaric, tartaric and trifluoroacetic acids.

The present invention is directed to the use of the compounds disclosed herein as inhibitors of β-secretase enzyme activity or n-site amyloid precursor protein-cleaving enzyme ("BACE") activity, in a patient or subject such as a mammal in need of such inhibition, comprising the administration of an effective amount of the compound. The terms "β-secretase enzyme," "β-site amyloid precursor protein-cleaving enzyme," and "BACE" are used interchangably in this specification. In addition to humans, a variety of other mammals can be treated according to the method of the present invention.

The present invention is further directed to a method for the manufacture of a medicament or a composition for inhibiting β-secretase enzyme activity in humans and animals comprising combining a compound of the present invention with a pharmaceutical carrier or diluent.

The compounds of the present invention have utility in treating Alzheimer's disease. For example, the compounds may be useful in treating dementia of the Alzheimer's type, including early stage, intermediate stage or late stage dementia of the Alzheimer's type. The compounds may also be useful in treating diseases mediated by abnormal cleavage of amyloid precursor protein (also referred to as APP), and other conditions that may be treated or prevented by inhibition of β-secretase. Such conditions include mild cognitive impairment, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, Down syndrome, pancreatitis, inclusion body myositis, other peripheral amyloidoses, diabetes and atherosclerosis.

The subject or patient to whom the compounds of the present invention is administered is generally a human being, male or female, in whom inhibition of β-secretase enzyme activity is desired, but may also encompass other mammals, such as dogs, cats, mice, rats, cattle, horses, sheep, rabbits, monkeys, chimpanzees or other apes or primates, for which inhibition of β-secretase enzyme activity or treatment of the above noted disorders is desired.

The compounds of the present invention may be used in combination with one or more other drugs in the treatment of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefor, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

Examples of combinations of the compounds of the present invention with other drugs in either unit dose or kit form include combinations with anti-Alzheimer's agents, for example other beta-secretase inhibitors; gamma-secretase inhibitors; HMG-CoA reductase inhibitors; NSAIDs including ibuprofen; vitamin E; anti-amyloid antibodies, including humanized monoclonal antibodies; CB-1 receptor antagonists or CB-1 receptor inverse agonists; antibiotics such as doxycycline and rifampin; N-methyl-D-aspartate (NMDA) receptor antagonists, such as mematine; cholinesterase inhibitors such as galantamine, rivastigmine, donepezil and tacrine; growth hormone secretagogues such as ibutamoren, ibutamoren mesylate and capromorelin; histamine $H_3$ antagonists; AMPA agonists, PDEIV inhibitors; $GABA_A$ inverse agonists; neuronal nicotinic agonists; or other drugs that affect receptors or enzymes that either increase the efficacy, safety, convenience, or reduce unwanted side effects or toxicity of the compounds of the present invention. The foregoing list of combinations is illustrative only and not intended to be limiting in any way.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by admixing a compound of the present invention and a pharmaceutically acceptable carrier.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Other pharmaceutical compositions include aqueous suspensions, which contain the active materials in admixture with excipients suitable for the manufacture of aqueous suspensions. In addition, oily suspensions may be formulated by suspending the active ingredient in a vegetable oil, for example arachis oil, olive oil, sesame oil or coconut oil, or in a mineral oil such as liquid paraffin. Oily suspensions may also contain various excipients. The pharmaceutical compositions of the invention may also be in the form of oil-in-water emulsions, which may also contain excipients such as sweetening and flavoring agents.

The pharmaceutical compositions may be in the form of a sterile injectable aqueous or oleagenous suspension, which may be formulated according to the known art, or may be administered in the form of suppositories for rectal administration of the drug.

The compounds of the present invention may also be administered by inhalation, by way of inhalation devices known to those skilled in the art, or by a transdermal patch.

By "pharmaceutically acceptable" it is meant the carrier, diluent or excipient must be compatible with the other ingredients of the formulation and not deleterious to the recipient thereof.

The terms "administration of" or "administering a" compound should be understood to mean providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The terms "effective amount" or "therapeutically effective amount" means the amount of the subject compound that will elicit the biological or medical response of a tissue, system, animal or human that is being sought by the researcher, veterinarian, medical doctor or other clinician. As used herein, the term "treatment" refers to the treatment of the mentioned conditions, particularly in a patient who demonstrates symptoms of the disease or disorder.

As used herein, the term "treating" means any administration of a compound of the present invention and includes (1) inhibiting the disease in an animal that is experiencing or displaying the pathology or symptomotology of the disease (i.e., arresting further development of the pathology and/or symptomatology), or (2) ameliorating the disease in an animal that is experiencing or displaying the pathology of symptomatology of the disease (i.e., reversing theathology and/or symptomatology). The term "controlling" includes preventing treating, eradicating, ameliorating or otherwise reducing the severity of the condition being controlled.

The compositions containing compounds of the present invention may conveniently be presented in unit dosage form and may be prepared by any of the methods well known in the art of pharmacy. The term "unit dosage form" is taken to mean a single dose wherein all active and inactive ingredients are combined in a suitable system, such that the patient or person adminstering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples in the pharmacy arts of unit dosage forms.

The compositions containing compounds of the present invention may conveniently be presented as a kit, whereby two or more components, which may be active or inactive ingredients, carriers, diluents, and the like, are provided with instructions for preparation of the actual dosage form by the patient or person adminstering the drug to the patient. Such kits may be provided with all necessary materials and ingredients contained therein, or they may contain instructions for using or making materials or components that must be obtained independently by the patient or person administering the drug to the patient.

When treating Alzheimer's disease or other diseases for which compounds of the present invention are indicated, generally satisfactory results are obtained when the compounds of the present invention are administered at a daily dosage of from about 0.1 mg to about 100 mg per kg of animal body weight, preferably given as a single daily dose or in divided doses two to six times a day, or in sustained release form. The total daily dosage is from about 1.0 mg to about 2000 mg, preferably from about 0.1 mg to about 20 mg per kg of body weight. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

Specific dosages of the compounds of the present invention, or pharmaceutically acceptable salts thereof, for administration include 1 mg, 5 mg, 10 mg, 30 mg, 100 mg, 300 mg and 500 mg. Pharmaceutical compositions of the present invention may be provided in a formulation comprising about 0.5 mg to 1000 mg active ingredient; more preferably comprising about 0.5 mg to 500 mg active ingredient; or 0.5 mg to 250 mg active ingredient; or 1 mg to 100 mg active ingredient. Specific pharmaceutical compositions may comprise about 1 mg, 5 mg, 10 mg, 30 mg, 100 mg, 300 mg and 500 mg of active ingredient.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The utility of the compounds in accordance with the present invention as inhibitors of β-secretase enzyme activity may be demonstrated by methodology known in the art. Enzyme inhibition is determined as follows.

FRET Assay: A homogeneous end point fluorescence resonance energy transfer (FRET) assay is employed with the substrate ([TAMRA-5-CO-EEISEVNLDAEF-NHQSY] QFRET), which is cleaved by BACE 1 to release the fluorescence from TAMRA. The Km of the substrate is not determined due to the limit of solubility of the substrate. A typical reaction contains approximately 30 nM enzyme, 1.25 µM of the substrate, and buffer (50 mM NaOAc, pH 4.5, 0.1 mg/ml BSA, 0.2% CHAPS, 15 mM EDTA and 1 mM deferoxamine) in a total reaction volume of 100 µl. The reaction is proceeded for 30 min and the liberation of TAMRA fragment is measured in a 96-well plate LJL Analyst AD using an excitation wavelength of 530 nm and an emission wavelength of 580 nm. Under these conditions, less than 10% of substrate is processed by BACE 1. The enzyme used in these studies was soluble (transmembrane domain and cytoplasmic extension excluded) human protein produced in a baculovirus expression system. To measure the inhibitory potency of compounds, solutions of inhibitor in DMSO (four concentrations of the inhibitors were prepared: 1 mM, 100 µM, 10 µM, 1 µM) were included in the reactions mixture (final DMSO concentration is 0.8%). All experiments were conducted at room temperature using the standard reaction conditions described above. To determine the $IC_{50}$ of the compound, competitive equation $V0/Vi=1+[I]/[IC50]$ was used to predict the inhibitory potency of the compounds. The errors in reproducing the dissociation constants are typically less than two-fold.

HPLC assay: A homogeneous end point HPLC assay is employed with the substrate (coumarin-CO-REVNFE-VEFR), which is cleaved by BACE 1 to release the N-terminal fragment attached with coumarin. The Km of the substrate is greater than 100 µM and can not be determined due to the limit of solubility of the substrate. A typical reaction contains approximately 2 nM enzyme, 1.0 µM of the substrate, and buffer (50 mM NaOAc, pH 4.5, 0.1 mg/ml BSA, 0.2% CHAPS, 15 mM EDTA and 1 mM deferoxamine) in a total reaction volume of 100 µl. The reaction is proceeded for 30 min and is stopped by the addition of 25 µL of 1 M Tris-HCl, pH 8.0. The resulting reaction mixture was loaded on the HPLC and the product was separated from substrate with 5 min linear gradient. Under these conditions, less than 10% of substrate is processed by BACE 1. The enzyme used in these studies was soluble (transmembrane domain and cytoplasmic extension excluded) human protein produced in a baculovirus expression system. To measure the inhibitory potency for compounds, solutions of inhibitor in DMSO (12 concentrations of the inhibitors were prepared and the concentration rage was dependent on the potency predicted by FRET) were included in the reaction mixture (final DMSO concentration is 10%). All experiments were conducted at room temperature using the standard reaction conditions described above. To determine the $IC_{50}$ of the compound, four parameters equation is employed for curve fitting. The errors in reproducing the dissociation constants are typically less than two-fold.

In particular, the compounds of the following examples had activity in inhibiting the beta-secretase enzyme in the aforementioned assay, generally with an $IC_{50}$ from about 1 nM to 100 μM. Such a result is indicative of the intrinsic activity of the compounds in use as inhibitors of beta-secretase enzyme activity.

Several methods for preparing the compounds of this invention are illustrated in the following Schemes and Examples. Starting materials are made according to procedures known in the art or as illustrated herein. The following examples are provided so that the invention might be more fully understood. These examples are illustrative only and should not be construed as limiting the invention in any way.

The following abbreviations are used throughout the text:
Ar: aryl
Ph: phenyl
Me: methyl
Et: ethyl
Ac: acetyl
t-bu: tert-butyl
Pyr: pyridine
TFA: trifluoroacetic acid
DMF: N,N'-dimethyl formamide
THF: tetrahydrofuran
LAH: lithium aluminum hydride
TFA: trifluoroacetic acid
DMSO: dimethylsulfoxide
HPLC: high performance liquid chromatography
EDTA: ethylene diamine tetraacetic acid
Boc: tert-butyloxy carbonyl
rac: racemic
MAL: diisobutylaluminium hydride
BOP: Benzotriazol-1-yloxy-tris(dimethylamino)phosphonium hexafluorophosphate
DEAD: diethylazole dicarboxylate Intermediate I: 2-amino-2-benzylpropane-1,3-diol

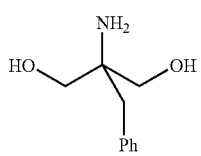

To a solution of rac-benzylserine (4.00 g, 20.49 mmol) in 60 mL THF at room temperature was added $NaBH_4$ (2.71 g 71.71 mmol) in one portion. The solution was fitted with a reflux condenser and cooled to 0° C. Iodine (7.80 g, 30.73 mmol) in 20 mL THF was added dropwise via cannula. After the addition was complete, the reaction was heated to reflux for 15 h. The reaction was then cooled to 0° C. and quenched by the addition of methanol until the bubbling subsided. The residue was acidified by the addition of 6N HCl until the pH was below one, then concentrated to afford 2-amino-2-benzylpropane-1,3-diol contaminated with inorganic residue. The unpurified reaction mixture was redissolved in methanol and filtered through a pad of celite (rinsing copiously with fresh methanol) to remove some of the insoluble inorganic residue. After concentration, further purification was accomplished using ion exchange chromatography (SCX catridge) to afford 2-amino-2-benzylpropane-1,3-diol I as a white solid. $^1$H NMR (400 MHz, $d_4$-MeOH) δ 7.34-7.25 (m, 5H), 3.52 (s, 4H), 3.00 (s, 2H).

Intermediate II: tert-butyl [1-benzyl-2-hydroxy-1-(hydroxymethyl)ethyl]carbamate

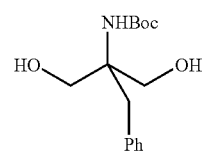

To a solution of 2-amino-2-benzylpropane-1,3-diol I (0.901 g, 4.971 mmol) in 50 mL THF was added di-tert-butyl dicarbonate (1.139 g, 5.22 mmol). After 14 h at room temperature, the reaction was concentrated, and purified by flash chromatography (40 g silica, 0->10% $MeOH/CH_2Cl_2$) to afford tert-butyl [1-benzyl-2-hydroxy-1-(hydroxymethyl)ethyl]carbamate II as a white solid. $^1$H NMR (400 MHz, $d_4$-MeOH) δ 7.25-7.15 (m, 5H), 3.59 (d, J=11.0 Hz, 2H), 3.54 (d, J=11.0 Hz, 2H), 2.98 (s, 2H), 1.449 (s, 9H).

Intermediate III: tert-butyl 2-hydroxy-1-(hydroxymethyl)-1-(thien-3-ylmethyl)ethylcarbamate

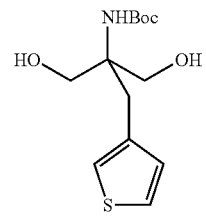

Step A: Alkylation

To a solution of diethyl 2-[N-(tert-butoxycarbonyl)-amino]malonate (1.44 mL, 5.65 mmol) in 30 mL EtOH cooled to 0° C. was added sodium ethoxide (2.22 mL, 5.93 mmol, 21% in EtOH). The reaction mixture was stirred at 0° C. for 5 min and 3-bromomethyl-thiophene (1 g, 5.65 mmol) in 10 mL EtOH was added dropwise. The reaction mixture was allowed to warm to room temperature over 14 h. The reaction mixture was quenched with water, and extracted with EtOAc. The organic layer was washed with brine, dried over sodium sulfate, concentrated in vacuo, and purified by flash chromatography (120 g silica, 0->25% EtOAc/hexanes) to afford diethyl 2,2-[N-(tert-butoxycarbonyl)-amino]-(thien-3-ylmethyl)malonate as a colorless oil. $^1$H NMR (400 MHz, $CDCl_3$) δ 7.22 (dd, J=4.8 Hz, 2.5 Hz, 1H), 6.94 (d, J=2.5 Hz, 1H), 6.81 (d, J=4.8 Hz, 1H), 5.82 (br s, 1H), 4.34-4.14 (m, 4H), 3.66 (s, 2H), 1.47 (s, 9H), 1.27 (t, J=7.2 Hz, 6H).

Step B: Reduction

A solution of diethyl 2,2-[N-(tert-butoxycarbonyl)-amino]-(thien-3-ylmethyl)malonate (1.52 g, 12.69 mmol) in 10 mL diethyl ether was added dropwise to LAH (12.7 mL, 12.7 mmol, 1M in diethyl ether) in 20 mL diethyl ether cooled to 0° C. The reaction mixture was stirred at 0° C. for 1.25 h. The reaction mixture was carefully quenched with water (0.48 mL), 15% NaOH (0.48 mL), water (1.45 mL), stirred vigorously at room temperature for 5 min, diluted with THF, filtered on cellite, rinsed with THF, dried over sodium sulfate, concentrated in vacuo, and purified by flash chromatography (120 g silica, 25->50% EtOAc/hexanes) to afford tert-butyl 2-hydroxy-1-(hydroxymethyl)-1-(thien-3-ylmethyl)ethyl-carbamate III as a thick colorless oil. $^1$H NMR (400 MHz, CD$_3$OD) δ 7.29 (dd, J=4.8 Hz, 3.2 Hz, 1H), 7.08 (dd, J=3.2 Hz, 0.8 Hz, 1H), 6.98 (dd, J=4.8, 0.8 Hz, 1H), 3.61 (A of AB, d, J=20.0 Hz, 2H), 3.55 (B of AB, d, J=20.0 Hz, 2H), 3.04 (s, 2H), 1.47 (s, 9H).

Intermediate IV: methyl alpha-(aminomethyl)-N-(tert-butoxycarbonyl)phenylalaninate

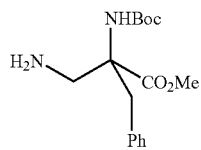

Step A: Hydroxy to Azide Conversion

To a solution of methyl N-(tert-butoxycarbonyl)-alpha-(hydroxymethyl)phenylalaninate (0.5 g, 1.62 mmol, prepared from benzylserine via esterification in MeOH and Boc installation (or according to A. Kozikowski et al, Bioorg. Med. Chem. Lett. 1998, 8, 447-452) in 10 mL THF was added hydrazoic acid (1.2 mL, 2.42 mmol, 2M in benzene), triphenylphosphine (0.42 g, 1.62 mmol), and diethylazodicarboxylate (0.28 mL, 1.78 mmol) in 5 mL THF dropwise. The reaction mixture was stirred at room temperature for 16 h, concentrated in vacuo and purified by flash chromatography (90 g silica, 0->20% EtOAc/hexanes) to afford N-(tert-butoxycarbonyl)-alpha-azidomethyl)phenylalaninate. $^1$H NMR (400 MHz, CDCl$_3$) δ 7.30-7.20 (m, 3H), 7.05-6.98 (m, 2H), 5.47 (br s, 1H), 4.33 (d, J=12.4 Hz, 1H), 3.78 (s, 3H), 3.61 (d, J=12.4 Hz, 1H), 3.51 (d, J=13.2 Hz, 1H), 2.96 (d, J=13.2 Hz, 1H), 1.48 (s, 9H).

Step B: Hydrogenation

To a solution of N-(tert-butoxycarbonyl)-alpha-azidomethyl)phenylalaninate (144 mg, 0.43 mmol) in 20 mL MeOH, purged with argon was added 10% Pd/C (15 mg) and the system was flushed with hydrogen. The reaction mixture was stirred at room temperature under 1 atm of hydrogen for 1 h. Filtration on cellite, rinsing with MeOH and concentration in vacuo provided methyl alpha-(aminomethyl)-N-(tert-butoxycarbonyl)phenylalaninate IV. NMR (400 MHz, CDCl$_3$) δ 7.30-7.20 (m, 3H), 7.08-7.02 (m, 2H), 5.45 (br s, 1H), 3.78 (s, 3H), 3.56 (br d, J=13.6 Hz, 1H), 3.50 (br d, J=13.2 Hz, 1H), 3.10 (d, J=13.2 Hz, 1H), 3.06 (d, J=13.6 Hz, 1H), 1.48 (s, 9H), 1.07 (br s, 1H).

Intermediate A: 3-(bromomethyl)-N-[(1R)-1-(4-fluorophenyl)ethyl]-5-[methyl(methylsulfonyl)amino]benzamide

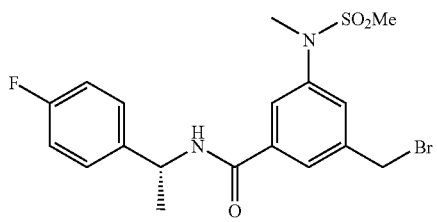

Step A: Sulfonylation

To a stirred slurry of dimethyl 5-aminoisophthalate (5.0 g, 23.90 mmol) in 100 mL CH$_2$Cl$_2$/pyridine (3:1) at 0° C. was added methanesulfonyl chloride (1.85 mL, 23.90 mmol). The resulting mixture was stirred for 4 h at room temperature. The solvent was removed in vacuo and ethylacetate (100 mL) was added resulting in precipitate formation. The product was collected by filtration to give the sulfonamide as a white solid. $^1$H NMR (DMSO$_{d6}$) δ 8.15 (s, 1H), 8.02 (s, 2H), 3.89 (s, 6H), 3.02 (s, 3H) LCMS [M-OCH$_3$1]=256.16.

Step B: Methylation

To a solution of sodium hydride (0153 g, 3.83 mmol, 60% oil dispersion) in 10 mL DMF was added sulfonamide (1.0 g, 3.48 mmol) from step A followed by methyl iodide (0.43 mL, 6.97 mmol). After 1 hr the reaction was quenched with H$_2$O (100 mL) and extracted with EtOAc (3×50 mL). The organic extracts were dried over MgSO$_4$ and evaporated to give the product. $^1$H NMR (DMSO$_{d6}$) δ 8.40 (s, 1H), 8.19 (s, 2H), 3.91 (s, 6H), 3.34 (s, 3H), 3.01 (s, 3H). LCMS [M+H]=302.15.

Step C: Hydrolysis

Diester (1.03 g, 3.38 mmol) from step B was dissolved in 50 mL THF:MeOH (1:1) and cooled to 0° C. 1N NaOH (3.38 mL, 3.38 mmol) was added and the reaction was allowed to warm to RT over 8 hours. The solution was acidified with 1N HCl (30 mL) and extracted with EtOAc (3×50 mL). The combined organic extracts were washed with brine and dried over MgSO$_4$, filtered and concentrated in vacuo. Purification on silica gel (5% MeOH/CHCl$_3$ containing 1% HOAc) gave the mono acid. $^1$H NMR (DMSO$_{d6}$) δ 8.30 (s, 1H), 8.10 (s, 2H), 3.84 (s, 3H), 3.27 (s, 3H), 2.94 (s, 3H). LCMS (M+H)=288.16.

Step D: Amine Coupling

A solution containing 0.133 g (0.46 mmol) of the monoacid from step C in 5 mL CH$_2$Cl$_2$, BOP reagent (0.235 g, 0.55 mmol), (R)-(+)-α-methylbenzylamine (0.071 mL, 0.55 mmol), and diisopropylamine (0.24 mL, 1.39 mmol) was stirred at ambient temperature for 1 h. Evaporation of the solvent and column chromatography on silica gel (90% EtOAc/Hexanes) afforded the benzyl amide. $^1$H NMR (CDCl$_3$) δ 8.26 (s, 1H), 8.17 (s, 1H), 8.06 (s, 1H), 7.31 (m, 5H), 6.50 (d, J=7.1 Hz, 1H), 5.33 (q, J=7.1 Hz, 1H), 3.96 (s, 3H), 3.37 (s, 3H), 2.88 (s, 3H), 1.64 (d, J=7.0 Hz, 3H). LCMS (M+H)=391.20.

Step E: Hydrolysis

To 0.171 g (0.438 mmol) of the benzyl amide from step D in 10 mL THF:MeOH (1:1) was added 2 N NaOH (0.66 mL, 1.32 mmol). The solution was heated to 50° C. for 1 h. After cooling the solution was acidified by the addition of 1 N HCl (20 mL) and extracted with EtOAc (3×30 mL). The combined organic extracts were dried over MgSO4, filtered, and concentrated in vacuo to yield the desired carboxylic acid. $^1$H NMR (CDCl$_3$) δ 8.22 (t, 1H), 8.11 (m, 1H), 8.06 (m, 1H), 7.34 (m, 5H), 6.47 (d, J=7.1 Hz, 1H), 5.33 (m, 1H), 3.37 (s, 3H), 2.87 (s, 3H), 1.64 (d, J=7.0 Hz, 3H). LCMS (M+H)=377.2.

Step E: Reduction

To a solution of acid from step D (800 mg, 2.0 mmol) in 20 mL THF cooled to 0° C. was added borane (6.0 ml, 6.0 mmol, 1 M in THF) dropwise. The reaction mixture was stirred at 0° C. for 20 min and at room temperature for 1 h 45 min. The reaction mixture was quenched with MeOH and stirred at room temperature for 16 h, and concentrated in vacuo. The residue was taken in EtOAc, washed with water, brine, dried over sodium sulfate and concentrated in vacuo to provide crude alcohol which was brominated as is in step F.

Step F: Bromination

To a solution of crude alcohol from step E (355 mg, 0.93 mmol) and carbon tetrabromide (0.4 g, 1.2 mmol) in 4.6 mL 1:1 CH$_3$CN:CH$_2$Cl$_2$ was added triphenylphosphine (0.29 g, 1.1 mmol) in 4.6 mL 1:1 CH$_3$CN:CH$_2$Cl$_2$ dropwise. After stirring at room temperature for 45 min, two additional batches of carbon tetrabromide and triphenyl phosphine (200 mg/150 mg and 20 mg/15 mg) were added at 30 min intervals, until the reaction appeared complete by LC/MS analysis. The reaction mixture was concentrated and purified by flash chromatography (40 g silica, 25->60% EtOAc/hexanes) to afford 220 mg of 3-(bromomethyl)-N-[(1R)-1-(4-fluorophenyl)

ethyl]-5-[methyl(methylsulfonyl)amino]benzamide A. ¹H NMR (400 MHz, CDCl₃) δ 7.73 (s, 1H), 7.65 (s, 1H), 7.57 (s, 1H), 7.32-7.40 (m, 2H), 7.09-7.01 (m, 2H), 6.32 (d, J=7.6 Hz, 1H), 5.36-5.24 (m, 1H), 4.50 (s, 2H), 3.36 (s, 3H), 2.78 (s, 3H), 1.62 (d, J=6.5 Hz, 3H).

Intermediate B: methyl 5-(bromomethyl)-2'-cyano-1,1'-biphenyl-3-carboxylate

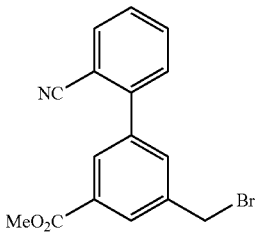

To a solution of dimethyl 5-iodoisophthalate (13 g, 40.6 mmol) in 100 mL THF was added 2-cyanophenyl zinc bromide (97.5 mL, 48.7 mmol, 0.5 M THF) and tetrakis(triphenylphosphine) palladium (214 mg, 0.2 mmol) and the reaction mixture was stirred at room temperature for 2 h. The precipitated solid was filtered, the filtrate was diluted with MeOH to provide after filtration of a second crop dimethyl 5-(2-cyanophenyl)isophthalate which was hydrolyzed to the corresponding monoacid 2'-cyano-5-(methoxycarbonyl)-1,1'-biphenyl-3-carboxylic acid following a similar procedure as described in intermediate A preparation, step C. ¹H NMR (400 MHz, d₆-DMSO) δ 13.55 (br s, 1H), 8.60-8.55 (m, 1H), 8.38-8.31 (m, 2H), 8.02 (d, J=8.3 Hz, 1H), 7.85 (td, J=8.3 Hz, 1.5 Hz 1H), 7.75 (d, J=8.3 Hz, 1H), 7.66 (td, J=8.3 Hz, 1.5 Hz 1H), 3.93 (s, 3H).

Reduction with borane and bromination using a similar procedure as described in intermediate A preparation, steps E and F afforded intermediate B: methyl 5-(bromomethyl)-2'-cyano-1,1'-biphenyl-3-carboxylate. NMR (400 MHz, CDCl₃) δ 8.12-8.18 (m, 2H), 7.83-7.77 (m, 2H), 7.69 (td, J=8.5 Hz, 1.4 Hz 1H), 7.55 (d, J=8.5 Hz, 1H), 7.51 (td, J=8.5 Hz, 1.4 Hz 1H), 4.59 (s, 2H), 3.96 (s, 3H).

EXAMPLE 1

3-[(2-amino-2-benzyl-3-hydroxypropoxy)methyl]-N-[(1R)-1-(4-fluorophenyl)ethyl]-5-[methyl(methylsulfonyl)amino]benzamide

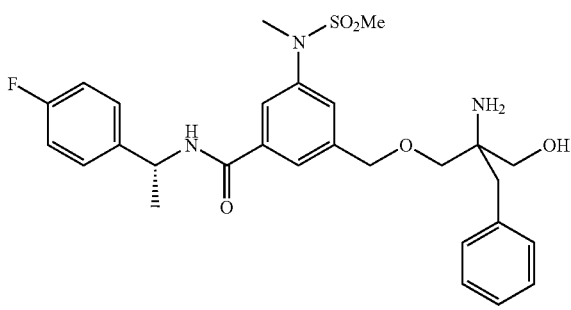

(1)

To a solution of intermediate I 2-amino-2-benzylpropane-1,3-diol (0.09 g, 0.50 mmol) in 2 mL DMF cooled to 0° C. was added sodium hexamethyldisylazide (0.5 mL, 0.50 mmol, 1 M in THF). The reaction mixture was stirred at 0° C. for 5 min and intermediate A 3-(bromomethyl)-N-[(1R)-1-(4-fluorophenyl)ethyl]-5-[methyl(methylsulfonyl)amino]benzamide (0.1 g, 0.23 mmol) in 1 mL DMF was added dropwise. The reaction mixture was stirred at 0° C. for 0.5 h, quenched with water, extracted with EtOAc, washed with aq LiCl (3×), dried over sodium sulfate, concentrated in vacuo, and purified by flash chromatography (40 g silica, 0->8% (10% NH₄OH in MeOH)/CH₂Cl₂) to afford 3-[(2-amino-2-benzyl-3-hydroxypropoxy)methyl]-N-[(1R)-1-(4-fluorophenyl)ethyl]-5-[methyl(methylsulfonyl)amino]benzamide. ¹H NMR (400 MHz, d₄-MeOH) δ 7.80 (s, 2H), 7.64 (s, 1H), 7.44-7.40 (m, 2H), 7.26-7.20 (m, 5H), 7.07-7.02 (m, 2H), 5.24 (q, J=7.0 Hz, 1H), 4.61 (s, 2H), 3.48 (A of AB, d, J=10.4 Hz, 1H), 3.43 (B of AB, d, J=10.4 Hz, 1H), 3.35 (s, 3H), 2.91 (s, 3H), 2.72 (A of AB, d, J=13.9 Hz, 1H), 2.66 (B of AB, d, J=13.9 Hz, 1H), 1.57 (d, J=7.0 Hz, 3H).

HRMS calculated for C₂₈H₃₄FN₃O₅S+H, 544.2276, found: 544.2275

EXAMPLE 2

3-{[2-amino-3-hydroxy-2-(thien-3-ylmethyl)propoxy]methyl}-N-[(1R)-1-(4-fluorophenyl)ethyl]-5-[methyl(methylsulfonyl)amino]benzamide

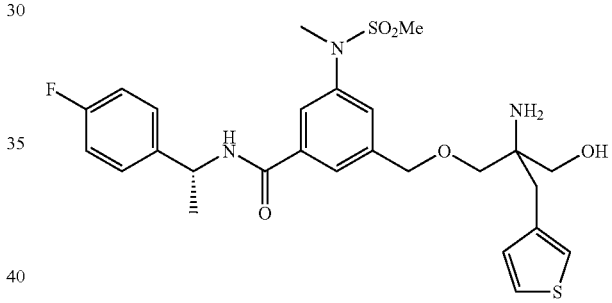

(2)

To a solution of intermediate A 3-(bromomethyl)-N-[(1R)-1-(4-fluorophenyl)ethyl]-5-[methyl(methylsulfonyl)amino]benzamide (50 mg, 0.11 mmol) in 1 mL CH₂Cl₂ cooled to 0° C. was added intermediate III tert-butyl 2-hydroxy-1-(hydroxymethyl)-1-(thien-3-ylmethyl)ethylcarbamate (81 mg, 0.28 mmol), silver triflate (72 mg, 0.28 mmol) and 2,6-ditert-butylpyridine (76 µL, 0.34 mmol). The reaction mixture was stirred at 0° C. for 40 min and purified by flash chromatography (20 g silica, 30->80% EtOAc/hexanes) and by preparative HPLC (5% to 95% CH₃CN in water containing 0.1% TFA, C18 PRO YMC 20×150 mm) to afford tert-butyl 2-({3-({[(1R)-1-(4-fluorophenyl)ethyl]amino}carbonyl)-5-[methyl(methylsulfonyl)amino]benzyl}oxy)-1-(hydroxymethyl)-1-(thien-3-ylmethyl) contaminated with 2,6-ditert-butylpyridine. Treatment with 10% TFA in CH₂Cl₂ for 30 min, followed by concentration under a stream of nitrogen, and purification by preparative HPLC (5% to 95% CH₃CN in water containing 0.1% TFA, C18 PRO YMC 20×150 mm) afforded 3-{[2-amino-3-hydroxy-2-(thien-3-ylmethyl)propoxy]methyl}-N-[(1R)-1-(4-fluorophenyl)ethyl]-5-[methyl(methylsulfonyl)amino]benzamide as a TFA salt. ¹H NMR (400 MHz, d₄-MeOH) δ 8.86 (d, J=7.9 Hz, 1H), 7.83 (s, 1H), 7.80 (s, 1H), 7.65 (s, 1H), 7.48-7.36 (m, 3H), 7.17 (s, 1H), 7.10-7.00 (m, 2H), 6.95 (d, J=5.0 Hz, 1H), 5.30-5.20 (m, 1H), 4.68 (A of AB, d, J=12.0 Hz, 1H), 4.63 (B of AB, d, J=12.0

Hz, 1H), 3.57 (s, 2H), 3.51 (A of AB, d, J=11.0 Hz, 1H), 3.45 (B of AB, d, J=11.0 Hz, 1H), 3.09 (s, 3H), 3.04 (A of AB, d, J=13.6 Hz, 1H), 3.45 (B of AB, d, J=13.6 Hz, 1H), 2.94 (s, 3H), 1.58 (d, J=7.1 Hz, 3H).

HRMS calculated for $C_{26}H_{32}FN_3O_5S_2$+H, 550.1840, found: 550.1814.

EXAMPLE 3

3-{[(2-amino-2-benzyl-3-hydroxypropyl)amino]methyl}-N-[(1R)-1-(4-fluorophenyl)ethyl]-5-[methyl(methylsulfonyl)amino]benzamide

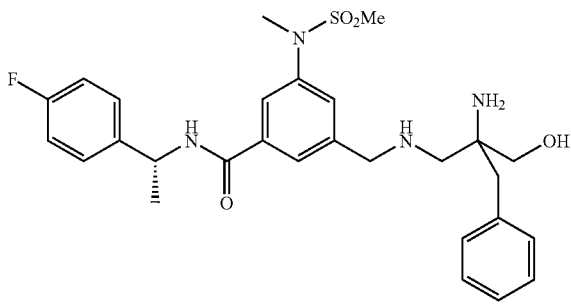

(3)

Step A: Alkylation of Intermediate IV with Bromide Intermediate A.

A solution of bromide intermediate A (102 mg, 0.23 mmol), amine intermediate IV (72 mg, 0.23 mmol) and potassium carbonate (35 mg, 0.25 mmol) in 1.5 mL DMF was stirred at room temperature for 16 h. The reaction mixture was diluted with EtOAc, washed with water (2×), brine, dried over sodium sulfate and concentrated in vacuo to provide crude methyl N-(tert-butoxycarbonyl)-alpha-[({3-({[(1R)-1-(4-fluorophenyl)ethyl]amino}carbonyl)-5-[methyl(methylsulfonyl)amino]benzyl}amino)methyl]-phenylalaninate which was used as is in step B.

Step B: Reduction of Methyl Ester

To a solution of crude methyl ester from step B (38 mg, 0.06 mmol) in 1 mL THF cooled to 0° C. was added LiBH$_4$ (0.14 mL, 0.29 mmol, 2 M THF) dropwise. The reaction mixture was allowed to warm to room temperature and progress was monitored by LC/MS. Additional portions of LiBH$_4$ were added over a period of 48 h to obtain disappearance of starting ester. The reaction mixture was quenched with acetone and MeOH and stirred at room temperature for 16 h. Concentration in vacuo and purification by flash chromatography (20 g silica, 50->100% EtOAc/hexanes, followed by 0->8% (10% NH$_4$OH in MeOH)/CH$_2$Cl$_2$) and by preparative HPLC (5% to 95% CH$_3$CN in water containing 0.1% TFA, C18 PRO YMC 20×150 mm) afforded tert-butyl 1-benzyl-2-({3-({[(1R)-1-(4-fluorophenyl)ethyl]amino}carbonyl)-5-[methyl(methylsulfonyl)amino]benzyl}amino)-1-(hydroxymethyl)ethylcarbamate which was deprotected as is in step C.

Step C: Boc Removal

Treatment of Boc derivative from step B with 50% TFA in CHCl$_3$ for 30 min, followed by concentration under a stream of nitrogen, and purification by preparative HPLC (5% to 95% CH$_3$CN in water containing 0.1% TFA, C18 PRO YMC 20×150 mm) afforded 3-{[(2-amino-2-benzyl-3-hydroxypropyl)amino]methyl}-N-[(1R)-1-(4-fluorophenyl)ethyl]-5-[methyl(methylsulfonyl)amino]benzamide as a bis TFA salt. $^1$H NMR (400 MHz, d$_4$-MeOH) δ 8.85 (d, J=7.9 Hz, 1H), 7.84 (s, 2H), 7.67 (s, 1H), 7.46-7.38 (m, 2H), 7.36-7.25 (m, 3H), 7.25-7.18 (m, 2H), 7.10-7.00 (m, 2H), 5.40-5.18 (m, 1H), 4.12-4.00 (m, 2H), 3.66 (A of AB, d, J=11.0 Hz, 1H), 3.61 (B of AB, d, J=11.0 Hz, 1H), 3.35 (s, 3H), 3.06-2.88 (m, 2H), 2.95 (s, 3H), 1.58 (d, J=7.1 Hz, 3H).

EXAMPLE 4

3'-[(2-amino-2-benzyl-3-hydroxypropoxy)methyl]-5'-{[2-(2-furyl)pyrrolidin-1-yl]carbonyl}-1,1'-biphenyl-2-carbonitrile

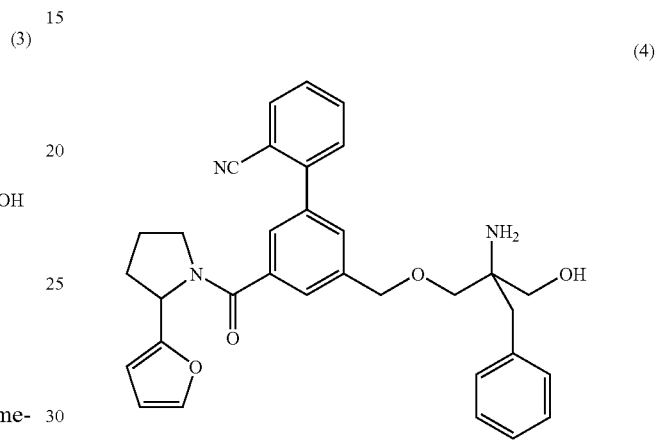

(4)

Step A: Alkylation of Intermediate II with Bromide Intermediate B.

Alkylation of tert-butyl [1-benzyl-2-hydroxy-1-(hydroxymethyl)ethyl]carbamate II with methyl 5-(bromomethyl)-2'-cyano-1,1'-biphenyl-3-carboxylate B using silver triflate and polymer-bound 2,6-ditert-butylpyridine polymer-bound following a similar procedure as described in example 2 provided methyl 5-({2-benzyl-2-[(tert-butoxycarbonyl)amino]-3-hydroxypropoxy}methyl)-2'-cyano-1,1'-biphenyl-3-carboxylate contaminated with product resulting from additional transesterification of the diol on the methyl ester. The mixture was used as is in step B.

Step B: Hydrolysis

To a solution of crude methyl 5-({2-benzyl-2-[(tert-butoxycarbonyl)-amino]-3-hydroxypropoxy}methyl)-2'-cyano-1,1'-biphenyl-3-carboxylate from step A (442 mg, 0.83 mmol) in 4 mL THF was added 1 N LiOH (1.25 mL, 1.25 mmol) and the reaction mixture was stirred at room temperature for 1.5 h. 1 N LiOH (1.25 mL, 1.25 mmol) was added and the reaction mixture was stirred at room temperature for 16 h. The reaction mixture was diluted with water, extracted with CH$_2$Cl$_2$ (3×), dried over sodium sulfate, concentrated in vacuo and purified by flash chromatography (90 g silica, 0->85% (0.5% HOAc in EtOAc)/hexanes) to provide 259 mg of 5-({2-benzyl-2-[(tert-butoxycarbonyl)amino]-3-hydroxypropoxy}methyl)-2'-cyano-1,1'-biphenyl-3-carboxylic acid as a colorless oil. $^1$H NMR (400 MHz, CDCl$_3$) δ 8.21 (s, 1H), 8.13 (s, 1H), 7.84 (s, 1H), 7.81 (d, J=7.7 Hz, 1H), 7.70 (t, J=7.3 Hz, 1H), 7.57 (d, J=7.7 Hz, 1H), 7.51 (t, J=7.3 Hz, 1H), 7.30-7.16 (m, 5H), 4.98 (s, 1H), 4.69 (A of AB, d, J=12.0 Hz, 1H), 4.65 (B of AB, d, J=12.0 Hz, 1H), 3.77 (A of AB, d, J=12.0 Hz, 1H), 3.69 (B of AB, d, J=12.0 Hz, 1H), 3.59 (A of AB, d, J=9.3 Hz, 1H), 3.69 (B of AB, d, J=9.3 Hz, 1H), 3.17 (A of AB, d, J=13.8 Hz, 1H), 2.93 (B of AB, d, J=13.8 Hz, 1H), 1.44 (s, 9H).

Step C: Coupling of $P_3$ Amine and Deprotection.

To a solution of acid from step B (20 mg, 0.04 mmol), 2-(2-furyl)pyrrolidine (16 mg, 0.12 mmol, WO 2000058283) and diisopropylethyl amine (0.017 mL, 0.1 mmol) in 0.5 mL DMF was added BOP reagent (0.021 mg, 0.05 mmol) and the reaction mixture was kept at room temperature for 0.25 h. Purification by preparative HPLC (5% to 95% $CH_3CN$ in water containing 0.1% TFA, C18 PRO YMC 20×150 mm) afforded tert-butyl 1-benzyl-2-[(2'-cyano-5-{[2-(2-furyl)pyrrolidin-1-yl]carbonyl}-1,1'-biphenyl-3-yl)methoxy]-1-(hydroxymethyl)ethylcarbamate as a TFA salt. Treatment with HCl(g) in $CH_2Cl_2$ for 16 h, followed by concentration under a stream of nitrogen, and purification by preparative HPLC (5% to 95% $CH_3CN$ in water containing 0.1% TFA, C18 PRO YMC 20×150 mm) and by flash chromatography (8 g silica, 0->20% (10% $NH_4OH$ in MeOH)/$CH_2Cl_2$) afforded 3'-[(2-amino-2-benzyl-3-hydroxypropoxy)methyl]-5'-{[2-(2-furyl)pyrrolidin-1-yl]carbonyl}-1,1'-biphenyl-2-carbonitrile. $^1H$ NMR (400 MHz, $d_4$-MeOH) ca. 1:1 rotomers mixture δ 9.91-7.12 (m, 13H), 6.34 (br s, 0.5H), 6.31 (br s, 0.5H), 6.14 (br s, 0.5H), 5.82 (br s, 0.5H), 5.42-5.36 (m, 0.5H), 5.13-5.05 (m, 0.5H), 4.67 (s, 1H), 4.59 (A of AB, d, J=12.8 Hz, 0.5H), 4.53 (B of AB, d, J=12.8 Hz, 0.5H), 3.85-3.73 (m, 1.5H), 3.65-3.54 (m, 0.5H), 3.50-3.40 (m, 2H), 2.80 (A of AB, d, J=13.2 Hz, 1H), 2.74 (B of AB, d, J=13.2 Hz, 1H), 2.38-2.00 (m, 4H).

LC/MS M+H=536.

The following compounds are prepared in a manner similar to the compounds of the foregoing examples using appropriate starting materials and reagents.

(5)

(6)

(7)

(8)

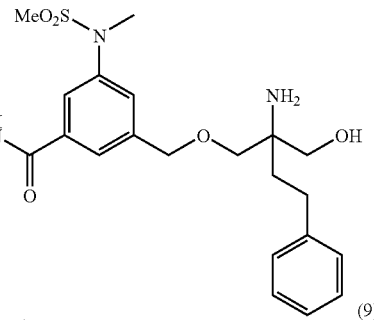

(9)

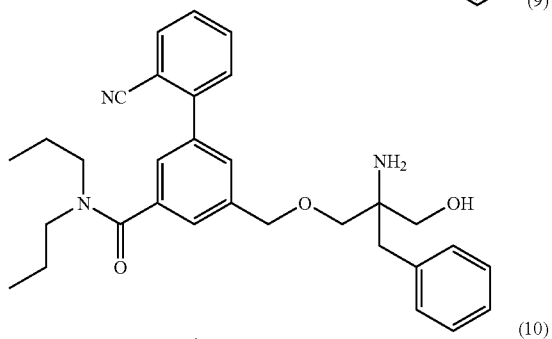

(10)

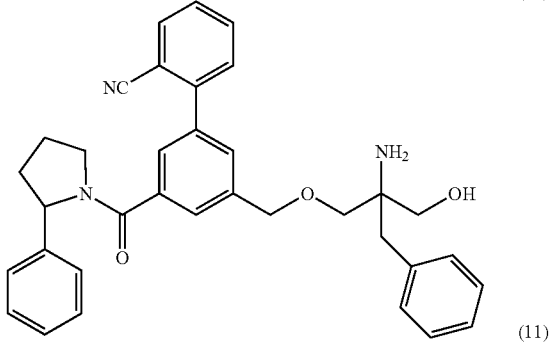

(11)

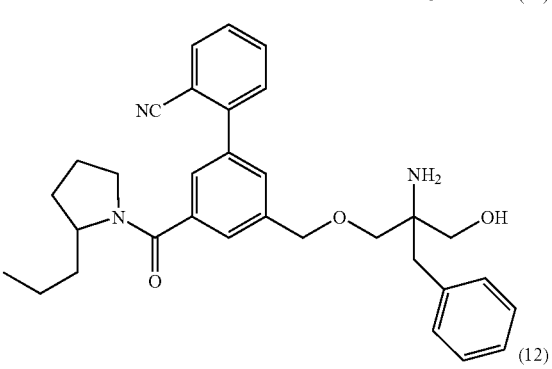

(12)

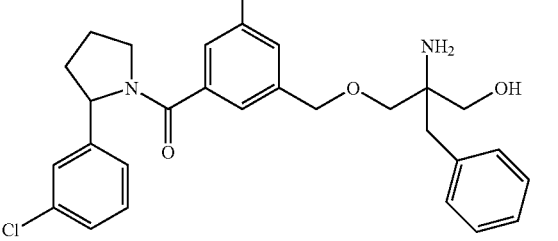

27
-continued

(13)
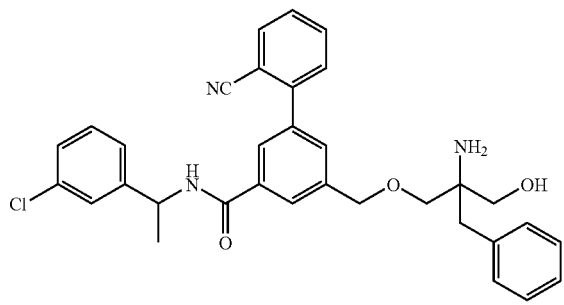

(14)
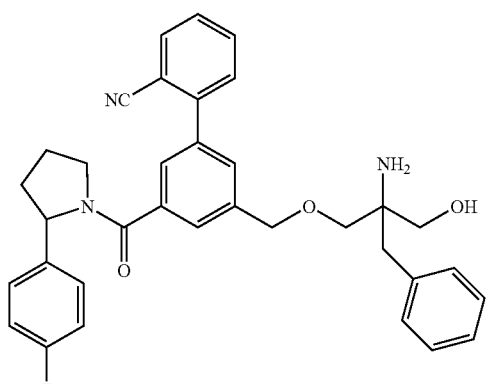

(15)
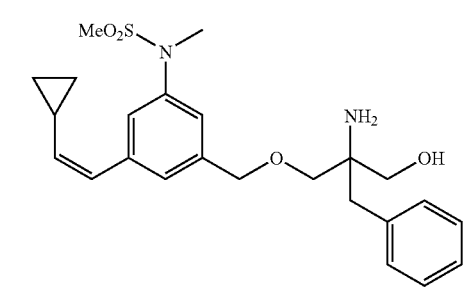

(16)
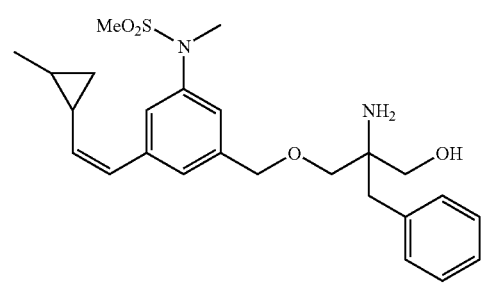

(17)
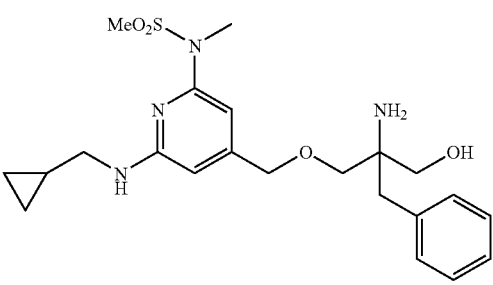

28
-continued

(18)
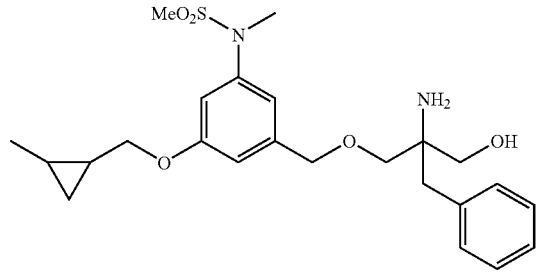

(19)
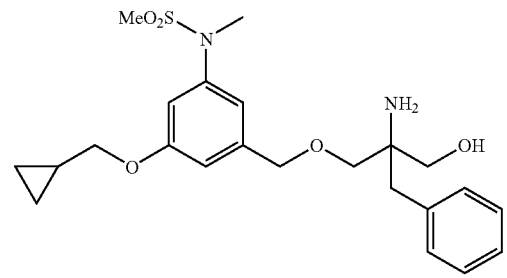

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

What is claimed is:

1. A compound of formula (I):

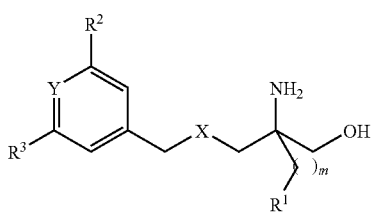

I wherein:
X is O or NH;
Y is N;
$R^1$ is (1) aryl selected from the group consisting of phenyl and napthyl, or
(2) heterocyclyl selected from the group consisting of piperazinyl, piperidinyl, pyrrolidinyl, pyrazinyl, dihydropyrazinyl, pyrazolyl, dihydropyrazolyl, pyridazinyl, pyridyl, dihydropyridinyl, pyrimidinyl, dihydropyrimidinyl, pyrrolyl, dihydropyrrolyl, tetrazolyl, dihydrotetrazolyl, furanyl, dihydrofuranyl, tetrahydrofuranyl, imidazolyl, dihydroimidazolyl, triazinyl, pyranyl, tetrahydropyranyl, thiazolyl, thienyl, dihydrothienyl, thiophenyl, triazolyl, dihydrotriazolyl, morpholinyl, thiomorpholinyl, dihydrothiadiazolyl, tetrahydrothienyl, oxazolyl, isoxazolyl, thiazolyl, oxadiazolyl, indolyl, quinolinyl, isoquinolinyl, benzimidazolyl and benzoxazolyl, wherein said aryl or heterocyclyl is unsubstituted or substituted with one or more
(a) halo,
(b) —$C_{1-6}$alkyl,
(c) —$C_{2-6}$ alkenyl,
(d) —$C_{2-6}$ alkynyl,
(e) —OH,
(f) —CN, or
(g) —O—$C_{1-6}$alkyl;

$R^2$ is selected from the group consisting of:
(1) $R^4$—S(O)$_2$N($R^7$)—, wherein $R^4$ is $C_{1-6}$alkyl, wherein said alkyl is unsubstituted or substituted with one or more
(a) halo,
(b) —$C_{2-6}$alkynyl,
(c) —OH,
(d) —CN, or
(e) —O—$C_{1-6}$alkyl; and $R^7$ is selected from the group consisting of
(a) hydrogen, and
(b) —$C_{1-6}$alkyl,
wherein said alkyl is unsubstituted or substituted with one or more
(i) halo,
(ii) —$C_{1-6}$alkyl,
(iii) —OH,
(iv) —CN, or
(v) —O—$C_{1-6}$alkyl;

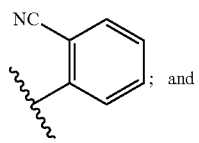 (2)
; and

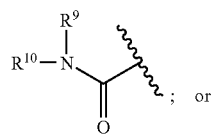 (3)

$R^3$ is selected from the group consisting of:

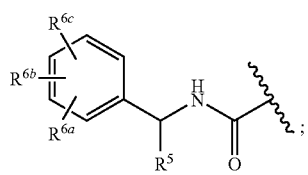
(a)

;

(b)

; or

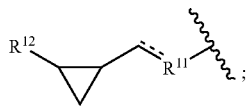 (c)

;

wherein $R^5$ is $C_{1-6}$alkyl, $C_{2-6}$ alkenyl or $C_{2-6}$ alkynyl;
$R^{6a}$, $R^{6b}$, and $R^{6c}$ are independently selected from the group consisting of:
(1) hydrogen,
(2) halo,
(3) —$C_{1-6}$alkyl,
(4) —$C_{2-6}$ alkenyl,
(5) —$C_{2-6}$ alkynyl,
(6) —OH,
(7) —CN, and
(8) —O—$C_{1-6}$alkyl;

$R^9$ and $R^{10}$ are independently selected from the group consisting of:
(1) hydrogen, and
(2) $C_{1-6}$alkyl,
(3) —$C_{2-6}$ alkenyl, and
(4) —$C_{2-6}$ alkynyl, or $R^9$ and $R^{10}$ are joined together with the nitrogen atom to which they are attached to form a pyrrolidine ring, which is optionally substituted with
(a) $C_{1-6}$alkyl,
(b) —$C_{2-6}$ alkenyl,
(c) —$C_{2-6}$ alkynyl,
(d) (CH$_2$)$_n$-phenyl, and
(e) (CH$_2$)$_n$-furanyl;
wherein said alkyl, phenyl and furanyl are unsubstituted or substituted with one or more
i) halo,
ii) —$C_{1-6}$alkyl,
iii) —OH,
iv) —CN, or
v) —O—$C_{1-6}$alkyl; and $R^{11}$ is selected from the group consisting of
(1) —CH—,
(2) —O—, and
(3) —NH—,
provided that when $R^{11}$ is —CH— the dotted line forms a bond and when $R^{11}$ is —O— or —NH— the dotted line is absent;

$R^{12}$ is hydrogen, $C_{1-6}$ alkyl, $C_{2-6}$ alkenyl or $C_{2-6}$ alkynyl;
m is 1 or 2;
n is 0, 1, 2, 3 or 4;
p is 1, 2, 3 or 4;
and pharmaceutically acceptable salts thereof.

2. The compound of claim 1, wherein m is 1 and $R^1$ is phenyl unsubstituted or substituted with one or more chloro or fluoro.

3. The compound of claim 1, wherein m is 2 and $R^1$ is phenyl unsubstituted or substituted with one or more chloro or fluoro.

4. The compound of claim 1, wherein m is 1 and $R^1$ is thiophenyl.

5. The compound of claim 1, wherein $R^2$ is ($R^4$)—S(O)$_2$N($R^7$)— and $R^7$ is $C_{1-6}$ alkyl.

6. The compound of claim 5 wherein $R^4$ and $R^7$ are each methyl.

7. The compound of claim 1, wherein $R^2$ is

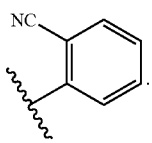

8. The compound of claim 1 wherein $R^3$ is

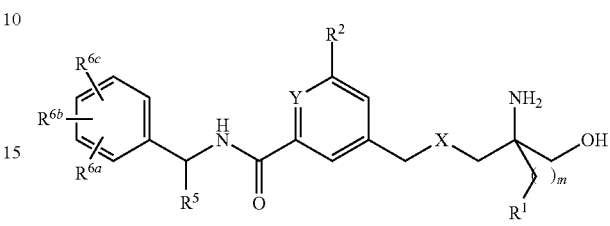

9. The compound of claim 8 wherein $R^5$ is methyl.

10. The compound of claim 9 wherein $R^{6a}$ and $R^{6c}$ are hydrogen and $R^{6b}$ is fluoro.

11. The compound of claim 10, wherein $R^3$ is

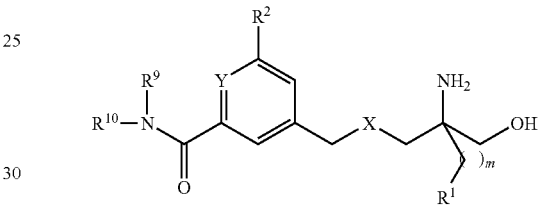

12. The compound of claim 1 wherein $R^3$ is

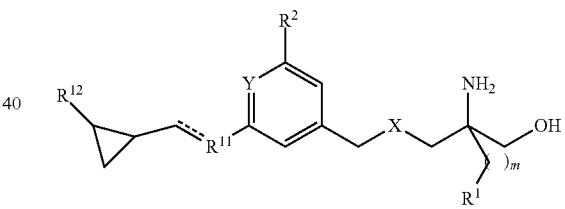

and $R^9$ and $R^{10}$ are joined together with the nitrogen atom to which they are attached to form a pyrrolidine ring which is unsubstituted or substituted with
 (a) $C_{1-6}$ alkyl,
 (b) $(CH_2)_n$-phenyl, or
 (c) $(CH_2)_n$-furanyl.

13. The compound of claim 12 wherein $R^9$ and $R^{10}$ are joined together with the nitrogen atom to which they are attached to form a pyrrolidine ring which is substituted with —$(CH_2)_n$— furanyl wherein n is 0.

14. The compound of claim 13, wherein $R^3$ is

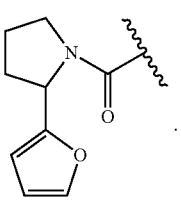

15. The compound of claim 1 wherein $R^3$ is

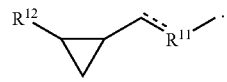

16. The compound of claim 1 of formula II:

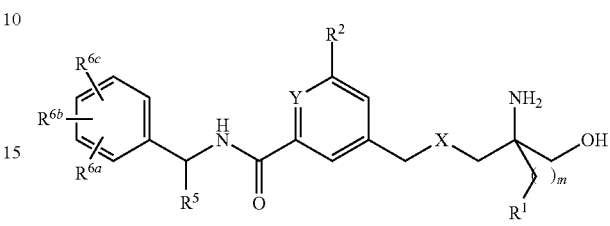

II wherein X, Y, $R^1$, $R^2$, $R^5$, $R^{6a}$, $R^{6b}$, $R^{6c}$ and m are as defined in claim 1.

17. The compound of claim 1 of formula (III):

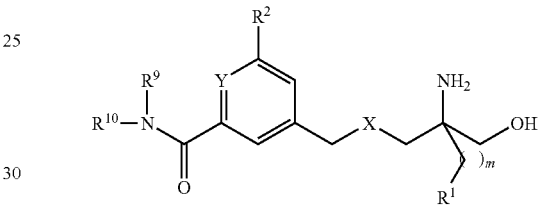

III wherein X, Y, $R^1$, $R^2$, $R^9$, $R^{10}$ and m are as defined in claim 1.

18. The compound of claim 1 of formula (IV):

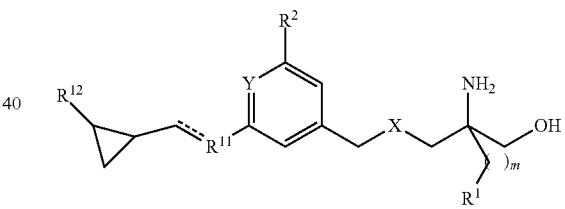

IV wherein X, Y, $R^1$, $R^2$, $R^{11}$, $R^{12}$ and m are as defined in claim 1.

19. A compound of claim 1 which is:

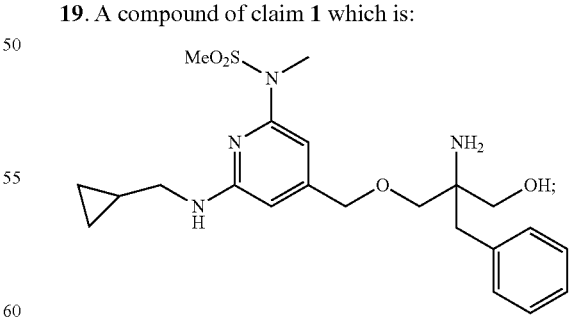

or a pharmaceutically acceptable salt thereof.

20. A pharmaceutical composition comprising an effective amount of a compound of claim 1 and a pharmaceutically acceptable carrier.

* * * * *